(12) United States Patent
Johansson et al.

(10) Patent No.: US 7,158,672 B2
(45) Date of Patent: Jan. 2, 2007

(54) RECIPE CALCULATION METHOD FOR MATT COLOR SHADES

(75) Inventors: Uwe Johansson, Erkrath (DE); Wilhelm Kettler, Wuppertal (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 791 days.

(21) Appl. No.: 10/459,202

(22) Filed: Jun. 11, 2003

(65) Prior Publication Data

US 2004/0252883 A1   Dec. 16, 2004

(51) Int. Cl.
   *G06K 9/00* (2006.01)
   *G06K 9/68* (2006.01)

(52) U.S. Cl. .................................... 382/167

(58) Field of Classification Search ........... 382/162, 382/164, 165, 167, 218, 305; 358/515, 518, 358/523, 530; 345/589–590, 600–604; 356/402, 356/405, 406–407, 425; 250/226
See application file for complete search history.

(56) References Cited

U.S. PATENT DOCUMENTS

| | | | |
|---|---|---|---|
| 2,838,413 A | 6/1958 | Young et al. | |
| 3,389,265 A | 6/1968 | Schreckendgust et al. | |
| 3,690,771 A | 9/1972 | Armstrong, Jr., et al. | |
| 3,712,745 A | 1/1973 | Armstrong, Jr., et al. | |
| 3,916,168 A | 10/1975 | McCarty et al. | |
| 4,479,718 A | 10/1984 | Alman | |
| 5,929,998 A | 7/1999 | Kettler et al. | |
| 6,064,487 A | 5/2000 | Kettler et al. | |

FOREIGN PATENT DOCUMENTS

WO   WO2002/11993 A1   2/2002

OTHER PUBLICATIONS

The International Search Report and Written Opinion of the International Searching Authority, Application No. PCT/US2004/019078, Mailed: Sep. 22, 2004.

*Primary Examiner*—Amir Alavi
(74) *Attorney, Agent, or Firm*—Sudhir G. Deshmukh (57) ABSTRACT

The present invention provides a color recipe calculation method for matt finished, solid color shades, by means of which it is possible to determine the proportion of matting agents in a color recipe in a manner decoupled from the actual calculation of the recipe and is based on a conventional spectrophotometric characterization of a matt sample using a standardised 45°/0° measurement geometry along with an established gloss measurement, or alternatively using a spectrophotometer equipped with a d/8° measurement geometry and analyzing readings taken with the specular component included and excluded.

10 Claims, 8 Drawing Sheets

RECIPE CALCULATION METHOD FOR MATT COLOR SHADES

FIELD OF THE INVENTION

The invention relates to a recipe calculation method for matt colour shades. The method is applied in the colour-imparting surface coating sector, in particular, for matching matt, solid, pigmented colour standards.

DESCRIPTION OF RELATED ART

Matching colour shades of unknown pigmentation may be considered a significant problem for all colouristics applications in a coatings company. In particular, in the vehicle coating sector, the range of pigments has seen continuous expansion in recent years. In the light of this development, implementing methods for minimizing effort when matching colour shades is of great economic importance.

Efficient matching of colour shades of unknown pigmentation in the colouristics laboratory is now assisted by computer-aided colour recipe calculation methods. Colour recipe calculation is a pigmentation analysis tool for colour shades making use of reflection spectroscopy in the visible range of the spectrum and utilizing a suitable radiative transport model to describe the diffusion of light in particulate media and thus, the instrumentally detectable reflection spectra. The Schuster-Kubelka-Munk theory is often used for opaquely pigmented, solid colour systems. Calculation of colour recipes generally involves making reference to pigment databases which store details of all pigments contained in available colourant systems with associated reflection data and optical material parameters. Reference may also be made to colour recipe databases when calculating colour correction recipes.

Apart from glossy colour shades, matt colour shades are also often used in colour-imparting surface coating. Few different methods of controlling the gloss-level of surface coatings are known. It is possible to matt a pigmented surface coating or to cover a glossy pigmented surface coating by a matt clear-coat layer. Adding a matting agent to a paint formulation is most frequently used to introduce the desired degree of surface structure into a polymeric material. These matting agents are homogeneously dispersed in the embedding medium; the effect of matting is achieved by some micro-heterogeneity inside the layer that produces an increase of diffuse light scattering from the sample surface. Different inorganic compounds as precipitated silica, kaolin, bentonite, or others are used as matting agents.

Since the determination of optical material parameters is a time- and cost-consuming procedure, it deems advantageous to formulate colour shades of different surface textures (glossy, semi-glossy, matt) using a common colourant system. In such a proceeding it is implicitly assumed that the characterization data determined for glossy colourants do not change very much when introducing some surface texture into the system, and that the resulting error in recipe calculation can be compensated by one or at most two additional correction steps. The time expenditure for the additional correction steps seems to be acceptable compared to the expenditure to determine optical material parameters for several colourant systems differing only by the degree of surface texture. In addition, working with only one colourant system provides the advantage of less stock-keeping units. However, the reduction of tinting steps in colour development is a permanent task.

No colour recipe calculation methods have hitherto been known which make reference to colour pigment or colour recipe databases for glossy colour shades and which, without entailing additional tinting steps, permit matt colour samples to be matched with acceptable quality.

There is accordingly a requirement for a colour recipe calculation method for matt colour samples which make it possible, on the basis of a colourant system for producing glossy colour shades, to obtain acceptably accurate results without entailing additional tinting steps.

SUMMARY OF THE INVENTION

The present invention provides a colour recipe calculation method for matt, solid colour shades, by means of which it is possible to determine the proportion of matting agents in a colour recipe in a manner decoupled from the actual calculation of the recipe.

The present invention accordingly relates to a colour recipe calculation method for matt solid colour standards, comprising the following steps:

A) acquiring the reflection spectrum of a matt, solid colour standard using one of the following measurement geometries:
   Aa) $45°/\epsilon°$—geometry with $\epsilon \geq 45°$,
   Ab) $d/8°$—geometry with the specular component included and calculated correction of the specular component, and optionally, determining the colourimetric positions ($L^*$, $a^*$, $b^*$) derived from the reflection spectrum, B1) matching the experimentally determined reflection spectrum, which has optionally been corrected for the specular component, using optical material parameters, stored in a pigment database, of the pigments of the available colourant system for the preparation of unmatted colour shades, so obtaining a colour recipe specifying the nature of the colour-imparting pigments and the concentration thereof or B2) comparing the experimentally determined reflection spectrum or the colourimetric positions derived therefrom with the colour recipes stored in a colour recipe database for unmatted colour shades with their associated reflection spectra or colourimetric positions derived therefrom and identifying from the colour recipe database a colour recipe specifying the nature of the colour-imparting pigments and the concentration thereof which comes closest to the colour standard, C) optionally, correcting the colour recipe obtained in B1) or B2) and adjusting the actual colour shade produced with the colour recipe obtained to the desired shade of the colour standard, D) measuring the degree of gloss of the matt, solid colour standard with a reflectometer conventional for gloss measurement at one or more gloss angles, E) determining the quantity of matting agent corresponding to the measured degree of gloss in the matt colour standard with the assistance of previously prepared calibration curves stored in a database for the available colourant system, which curves represent the degree of gloss measured at one or more gloss angles as a function of the quantity of matting agent in a colour recipe and F) obtaining a colour recipe to match the matt colour standard, which recipe contains the quantity of matting agent in addition to the colour recipe obtained in B1) or B2).

Alternatively the present invention relates to a colour recipe calculation method for matt solid colour standards, comprising the following steps:

A) acquiring the reflection spectrum of a matt, solid colour standard using the following measurement geometry:
   Ac) d/8°—geometry with the specular component included and with the specular component excluded and optionally determining the colourimetric positions (L*, a*, b*) derived from the reflection spectrum,
B1) matching the experimentally determined reflection spectrum with the specular component included, which has been corrected for the specular component, using optical material parameters, stored in a pigment database, of the pigments of the available colourant system for the preparation of unmatted colour shades, so obtaining a colour recipe specifying the nature of the colour-imparting pigments and the concentration thereof, or
B2) comparing the experimentally determined reflection spectrum with the specular component included, which has been corrected for the specular component or the colourimetric positions derived therefrom with the colour recipes stored in a colour recipe database for unmatted colour shades with their associated reflection spectra or colourimetric positions derived therefrom and identifying from the colour recipe database a colour recipe specifying the nature of the colour-imparting pigments and the concentration thereof which comes closest to the colour standard,
C) optionally, correcting the colour recipe obtained in B1) or B2) and adjusting the actual colour shade produced with the colour recipe obtained to the desired shade of the colour standard,
D1) acquiring the difference reflection spectrum of the reflection spectrum with the specular component included and the reflection spectrum with the specular component excluded,
E1) determining the quantity of matting agent corresponding to the difference reflection spectrum with the assistance of previously prepared calibration curves stored in a database for the available colourant system, which curves represent the functional relationship between difference reflection spectrum and the quantity of matting agent in a colour recipe
F) obtaining a colour recipe to match the matt colour standard, which recipe contains the quantity of matting agent in addition to the colour recipe obtained in B1) or B2).

DETAILED DESCRIPTION OF THE EMBODIMENTS

It has been found that, when comparing a glossy colour shade with a matt colour shade, the two colour shades may be distinguished instrumentally, for example by means of a goniospectrophotometer, only with difficulty if the 45°/45° measurement geometry is used. This means that, for this measurement geometry, the influence of surface (gloss, degree of surface roughness) on the reflection values and the colour positions derived therefrom is almost negligible, and that the matting agent content may accordingly be determined in a decoupled manner from the actual calculation of the recipe.

A decisive advantage of the present invention is accordingly that only one data set of optical material parameters or of colour recipes, namely that for the glossy coating, is required for graduated degrees of gloss or matting.

The individual steps of the method according to the invention are explained in greater detail below.

The starting point is a matt, solid colour standard which is to be matched or for the matching of which a suitable colour recipe is to be developed. First of all, in accordance with step A) of the method according to the invention, the reflection spectrum of the matt colour standard is acquired over a defined wavelength range. The reflection spectrum is preferably acquired over a wavelength range from 400–700 nm. One of the above-defined measurement geometries Aa) or Ab) is used for this purpose.

The measurement geometry according to Aa) may be subdivided as follows:
   1. 45°/$\epsilon$ where $\epsilon \geq 45°$, angle-dependent measurement with a goniospectrophotometer and
   2. 45°/$\epsilon$ where $\epsilon = 45°$, angle-independent measurement with a spectrophotometer.

The angle $\epsilon$ is the effective angle which relates to the angle of observation and is equal to the sum of the incident angle and observation angle. The definitions of corresponding measurement geometries and angles are known to the person skilled in the art. The following definitions are briefly outlined below for clarity's sake:

Definition of Measurement Geometries

Figure 1:
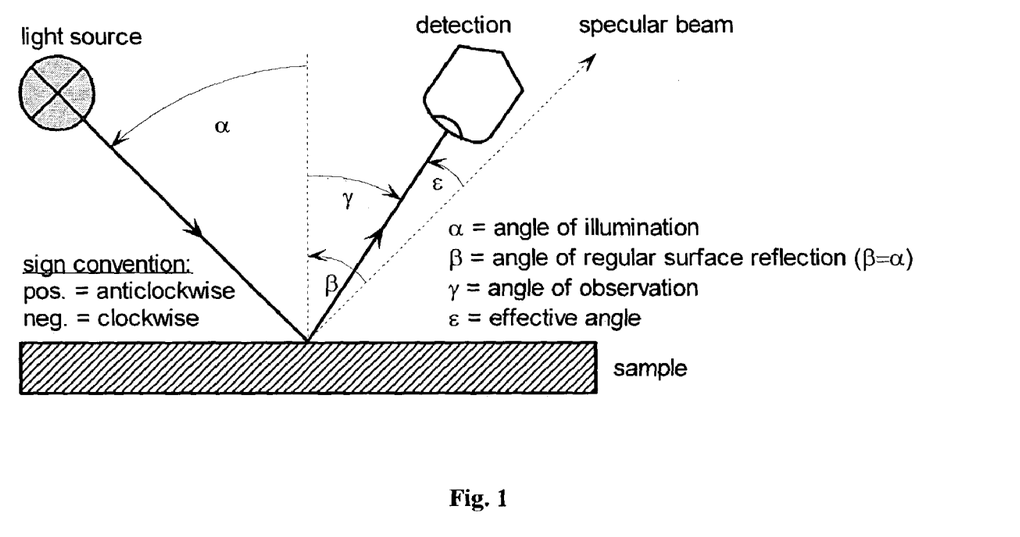
FIG. 1: Definition of measurement geometries realized in goniospectrophotometers.

FIG. 1 depicts the convention concerning the definitions of angles realized in commercial colour measurement systems.

The (positive) angle ($\alpha$) is measured between the surface normal and the light beam originating from the light source. The second angle of regular (surface) reflection ($\beta$) is equal to the angle of illumination, but situated on the other side of the surface normal (angle of incidence=angle of reflection). The third angle of observation ($\gamma$) is measured from the surface normal with positive sign if illumination and observation are on the same side and negative sign otherwise. The effective angle ($\epsilon$) is referred to the specular beam and is therefore equal to the sum of angles of illumination and observation, i. e. $\epsilon=\alpha+\gamma$. It is common practice to denote the measurement geometry, depicted in FIG. 1, by 45°/$\epsilon$.

The measurement geometry according to Aa)1. is based on collimated illumination at 45° (angle of incidence) and directed observation at variable angles of observation where $\epsilon \geqq 45°$. Conventional angles $\epsilon$ at which goniospectrophotometer readings can be taken and which correspond to the stated condition are, for example: 45°, 75°, 110°.

The measurement geometry according to Aa)2. is based on collimated illumination at 45° (angle of incidence) and directed observation at an angle of observation of 0°. In this case, the 45°/0° measurement geometry on the spectrophotometer corresponds to the 45°/45° measurement geometry on the goniospectrophotometer and in the present document will also be referred to as a 45°/45° geometry in order to permit a uniform definition.

The measurement geometry corresponding to Ab) is based on diffuse illumination (with the assistance of an Ulbricht sphere) and directed observation at an angle of 8° with respect to the sample normal (d/8°). In the present case of the matt colour sample, the measurement is made including the specular component and the specular component is taken into account by calculation. The spectra from which the specular component has been eliminated may then be formulated as usual with the data set of optical material parameters determined for a set of glossy calibration panels.

The above-mentioned measurement geometries are exhaustively described in the specialist literature, are familiar to the person skilled in the art of colour measurement, and are implemented in known conventional instruments.

Figure 2:
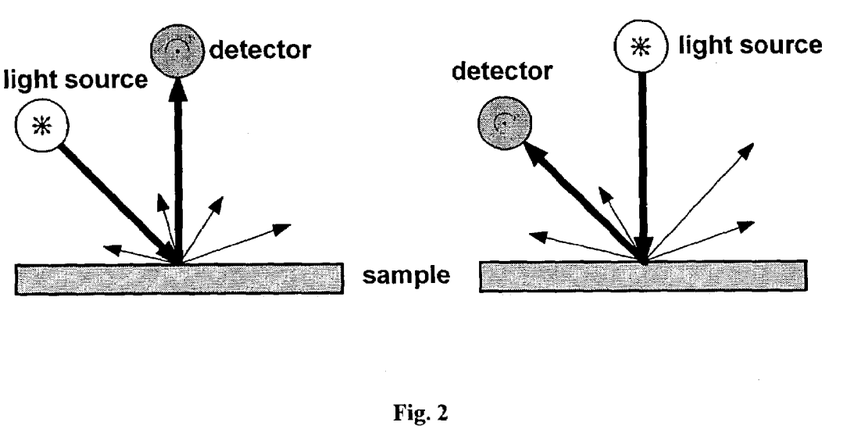
FIG. 2: Standard 45°/0° and 0°/45° measurement geometries, respectively, recommended by technical standards (as, e.g., DIN 5033) to be used for glossy and matt solid colour shades.
Figure 3:
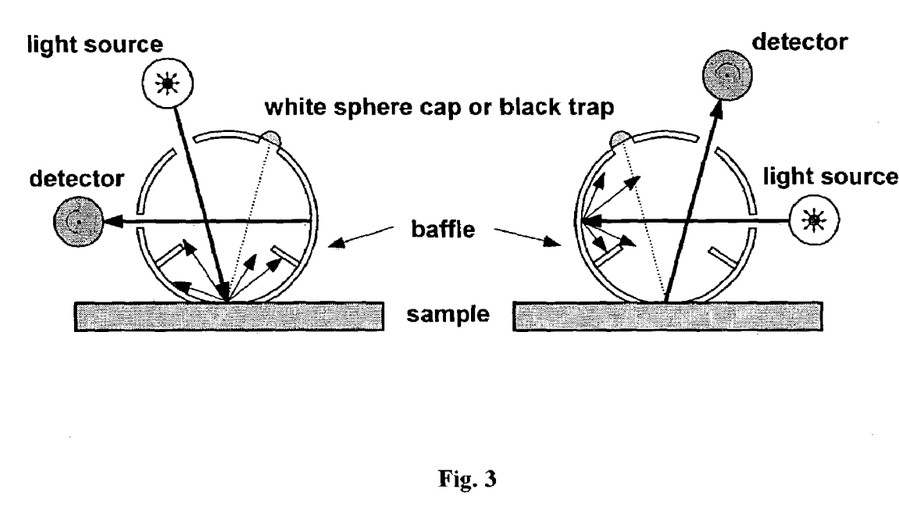
FIG. 3: Standard d/8° and 8°/d measurement geometries, respectively, recommended by technical standards (as, e.g., DIN 5033) to be used for glossy and matt solid colour shades.
Figure 4:
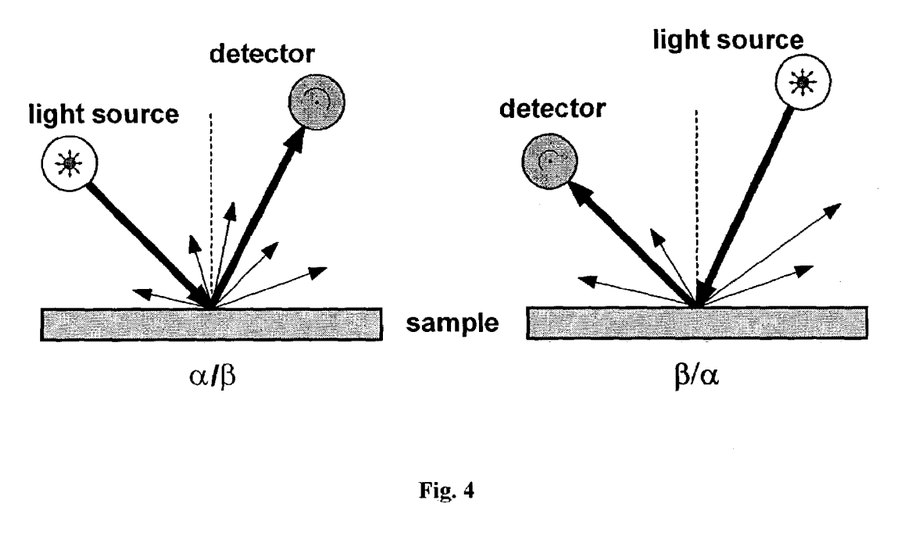
FIG. 4: Measurement geometry $\alpha/\beta$ or $\beta/\alpha$ suitable for glossy goniochromatic colour shades (not yet standardized, but established in industrial applications).

Measurement geometries/instruments may here be used with modulation of illumination or with modulation of observation (switching of illumination and observation component, i.e. reversal of beam path). Measurement geometries according to Aa)2. and Ab) are moreover stated, for example, in standard DIN 5033. Measurement geometries Aa)1., Aa)2. and Ab) are illustrated in FIGS. 2–4.

If required for further processing, the colourimetric positions (L*, a*, b*) may be determined in a conventional manner known to the person skilled in the art of colour measurement on the basis of the reflection spectrum of the matt colour standard experimentally determined in step A).

Depending upon which initial database is accessed, step B) of the method according to the invention involves either B1) matching the measured reflection spectrum, optionally corrected for surface gloss, of the colour standard so obtaining the colour recipe specifying the nature of the colour-imparting pigments to be used and the concentration thereof or B2) comparing the measured reflection spectrum of the colour standard with the colour recipes stored in a colour recipe database for glossy colour shades with their associated reflection spectra and identifying from the colour recipe database a colour recipe specifying the nature of the colour-imparting pigments and the concentration thereof which comes closest to the colour standard.

Step B1) or B2) of the method according to the invention proceeds in accordance with the art using discrete colouring pigment databases or colour recipe databases containing the required optical material parameters. It is advantageous according to the invention that it is possible to access colourant systems or colour recipes as are used for producing glossy colour samples.

The optical material parameters describe the properties of the colouring pigments when dispersed in the particular binder system. The parameters are pigment-specific and wavelength-dependent and must be determined for each desired wavelength by means of a set of appropriate calibration panels. To this end, a specific set of opaque calibration panels is produced for each colouring pigment and the reflection spectra are measured at the desired illumination and observation geometry. The optical material parameters are determined by fitting the radiative transport equation to the reflection factors experimentally determined for each pigment. In the case of the present solid colouring pigments, the known Schuster-Kubelka-Munk approximation to the radiative transport equation is sufficient. Using this approximation, it is possible to derive a simple relationship between the reflection R of an opaque surface coating and the scattering (S) and absorption properties (K) of the colouring pigments contained in said coating. The scattering and absorption coefficients are here obtained by adding together the individual contributions, weighted for the particular concentration, made by the various different colouring pigments.

After step B1) or B2), it is optionally additionally possible, if necessary, to correct the produced or identified colour recipe and to adjust the actual colour shade produced with the produced or identified colour recipe to the desired shade of the colour standard (step C).

In step D) of the method according to the invention, the degree of gloss of the matt, plain colour standard is measured with a reflectometer conventional for gloss measurement at one or more gloss angles, for example at 20°, 60° or 85°. Details of the measurement and evaluation procedures are concisely described in national and international standards (EN ISO 2813, ASTM D523, ASTM D5307, DIN 67530).

In step E), the quantity of matting agent corresponding to the measured degree of gloss in the matt colour standard is determined with the assistance of previously prepared calibration curves for the available colourant system. The calibration curves were prepared by previously measuring the degree of gloss at one or more gloss angles of calibration series containing differing quantities of matting agents and plotting the degree of gloss as a function of matting agent concentration.

Should various matting agents be used in the available colourant system, corresponding calibration curves must be produced for each matting agent.

As a result (step F)), a colour recipe is ultimately obtained which contains, in addition to the colour recipe obtained in B1) or B2), the quantity of matting agent. The colour recipe obtained in B1) or B2) and the determined quantity of matting agent may here be output separately or the determined quantity of matting agent is directly suitably incorporated into the previously determined colour recipe.

Obviously, when performing steps A) to F) of the method according to the invention, the stated sequence is not mandatory. For example, it is accordingly possible initially to perform steps D) and E) (determination of degree of gloss and matting agent concentration) and subsequently to measure reflection and determine colour recipes (steps A) to C)). Moreover, any optionally required correction of the colour shade produced with the determined colour recipe (step C)) may also not be performed until after the complete recipe, including the matting agent content, has been obtained. It is likewise obvious that the obtained degree of gloss/matting may, if necessary, also be corrected by adjusting the matting agent concentration.

Figure 5:
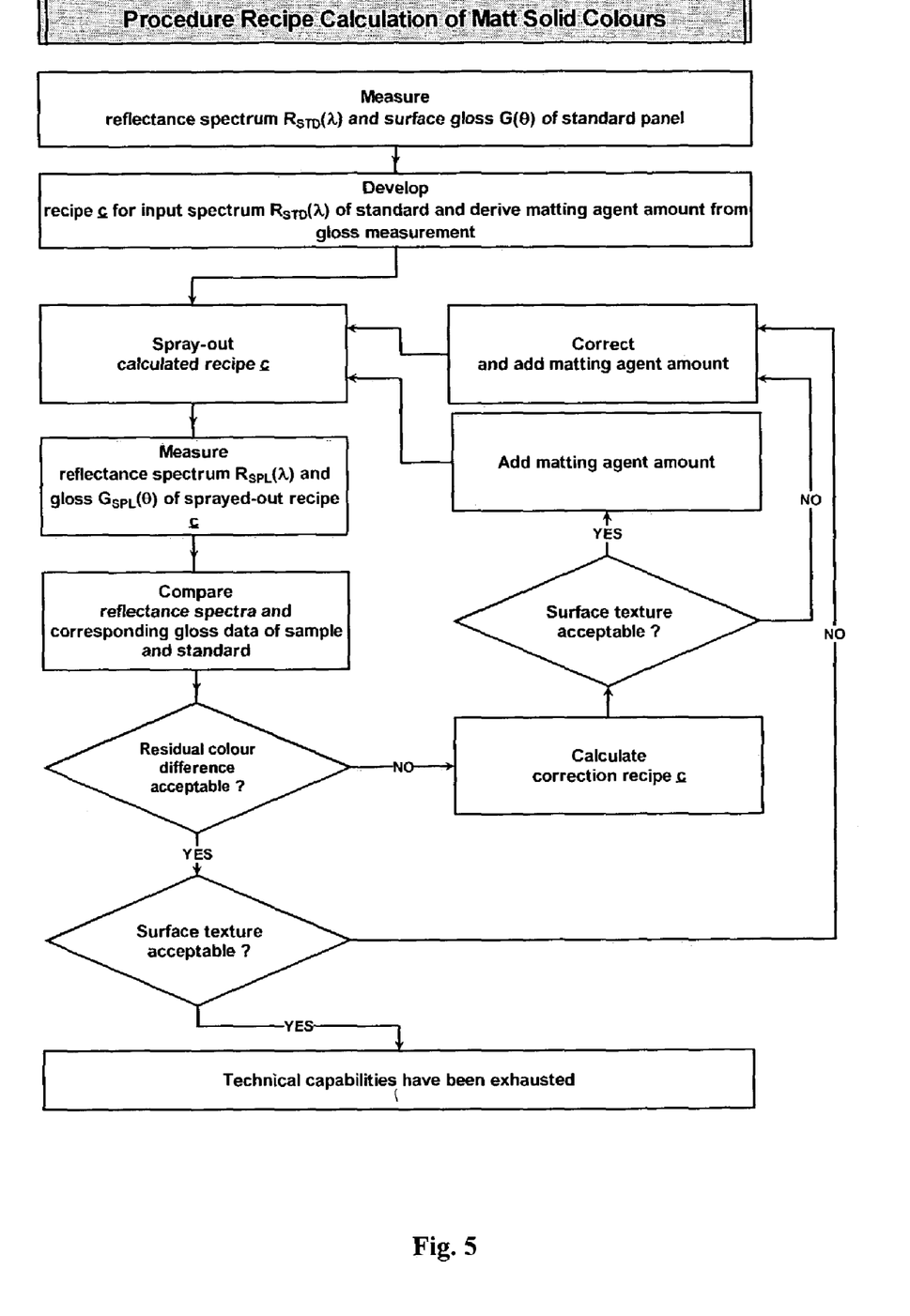
FIG. 5: Flow chart diagram of colour development process for matt solid colours.

FIG. 5 is a flow chart showing the relevant steps in a process using the invention of matching matt solid colours for the case of using a measurement geometry with a collimated beam path. In the first step, the reflectance properties of the standard to be matched are measured by means of a spectrophotometer. In addition, the surface gloss is characterized using a commercial gloss-meter. In the following step, the reflectance spectrum or the colour position of the standard is matched using the colourant assortment of the desired paint quality and the corresponding set of optical material parameters derived from an appropriate radiative transfer model, and the amount of matting agent generated from the gloss calibration curves. This colour matching step can be carried out interactively, where the user defines the pigmentation and the matching algorithm determines the corresponding optimum amounts, or automatically by means of a combinatorial procedure with appropriate control structures. Afterwards, the calculated recipe is mixed and sprayed-out. The optical properties (reflectance, gloss) of the dried panel are measured and the spectral and/or colour position results compared with the corresponding data of the standard. If the residual colour difference or the gloss of the specimen does not meet the specifications, the required corrections to the chromatic ingredients and to the matting agent have to be applied. The corrected recipe is again mixed and sprayed-out and compared to the standard. The process is terminated when all specifications are met or the instrumental capabilities are exhausted.

According to the alternative colour recipe calculation method of the present invention described above in step A) a spectrophotometer equipped with a d/8° measurement geometry is used with the specular component included and excluded.

The d/8° measurement geometry provides generally the option to take measurements with the specularly reflected component included (SPIN) or excluded (SPEX). In case of glossy samples, the difference of both spectra, $\Delta R=R(SPIN)-R(SPEX)$, solely depends on the refractive index n of the embedding medium. With increasing degree of surface roughness this difference gradually diminishes down to zero for ideally matt samples. Thus, this difference spectrum, $\Delta R$, is a measure of the degree of surface roughness. The functional relationship between difference spectrum, $\Delta R$, and matting agent concentration, $C_{M^A}$, can be calibrated by means of a set of calibration panels covering the possible range of surface roughness for a given paint system. To provide unique results this function has to decrease monotonously with increasing matting agent content. Once this $\Delta R=f(C_{M^A})$ function is available, it can be used to determine the matting agent content from the difference spectrum $\Delta R$ of a sample to be matched.

Figure 8:
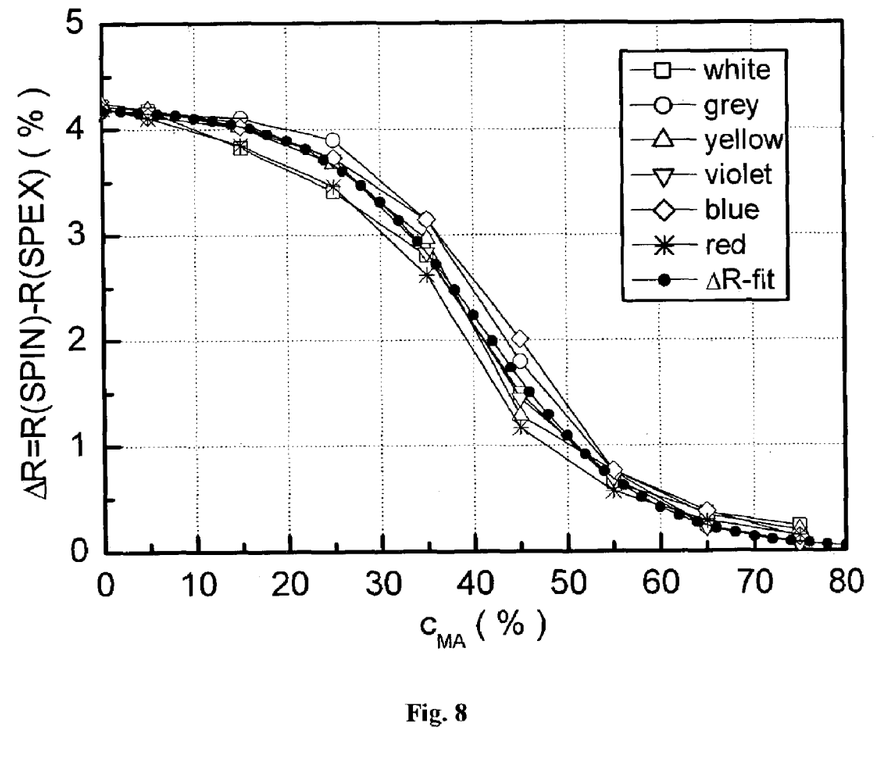
FIG. 8: Difference spectra, $\Delta R = R(SPIN) - R(SPEX)$, as recorded by a spectrophotometer equipped with a d/8° measurement geometry, for a selection of solid colours as a function of matting agent content, $C_{MA}$.

FIG. 8 exemplary shows calibration curves obtained for a selection of several solid colours of a conventional solvent-based industrial paint system as a function of matting agent content, $C_{M^A}$. The depicted experimental data represent wavelength-averaged quantities. In general, the $\Delta R(\lambda)$-functions slightly decrease with increasing wavelength by about 5% between 400 and 700 nm. A close scrutiny of FIG. 8 reveals that the functional relationship $\Delta R(C_{M^A})$ is monotonously decreasing with increasing matting agent concentration and can be inverted uniquely. Only the concentration range $20\% \leq C_{M^A} \leq 65\%$ is sufficiently sensitive for this purpose, while above and below this interval the slope of the $\Delta R(C_{M^A})$ curve approaches zero. However, only this concentration range is important for practical applications. According to FIG. 8, the average uncertainty in determining the matting agent content is ±3%. The curves depicted in FIG. 8 represent the profile of the particular instrument used for the measurements and may look different for other spectrophotometers.

Accordingly, the alternative colour recipe calculation method of the present invention described above requires in step D1) to acquire the difference reflection spectrum of the reflection spectrum with the specular component included and the reflection spectrum with the specular component excluded and in step E1) to determine the quantity of matting agent corresponding to the difference reflection spectrum with the assistance of previously prepared calibration curves stored in a database for the available colourant system, which curves represent the functional relationship between difference reflection spectrum and the quantity of matting agent in a colour recipe The matting agents used in the method according to the invention comprise conventional products, which are familiar to the person skilled in the art of colour development and are generally commercially available. The matting agent may be inorganic or organic in nature. Examples of inorganic matting agents are amorphous or pyrogenic silica, silica gels and phyllosilicates, for example, hydrated magnesium silicate (talcum). The inorganic matting agents may be present in untreated form or in a form surface-treated with organic compounds, for example, with suitable grades of wax, or also with inorganic compounds. Examples of organic matting agents are Al, Zn, Ca or Mg stearate, waxy compounds, such as for example micronized polypropylene waxes, together with urea/formaldehyde condensation products.

The colouring pigments used in the method according to the invention comprise conventional inorganic and/or organic absorption pigments, as are used in coating production. Examples of inorganic or organic colouring pigments are titanium dioxide, iron oxide pigments, carbon black, azo pigments, phthalocyanine pigments, quinacridone or pyrrolopyrrole pigments.

The following Examples illustrate the invention in greater detail:

EXAMPLES

The first step in using the proposed method in colour development is to calibrate the optical behaviour of all colourants of a pigment assortment using an appropriate mixture model like the Schuster-Kubelka-Munk theory and to determine the universal gloss=$f(C_{MA})$ functions between gloss and matting agent (MA) content for the recommended angle geometries.

Figure 6:
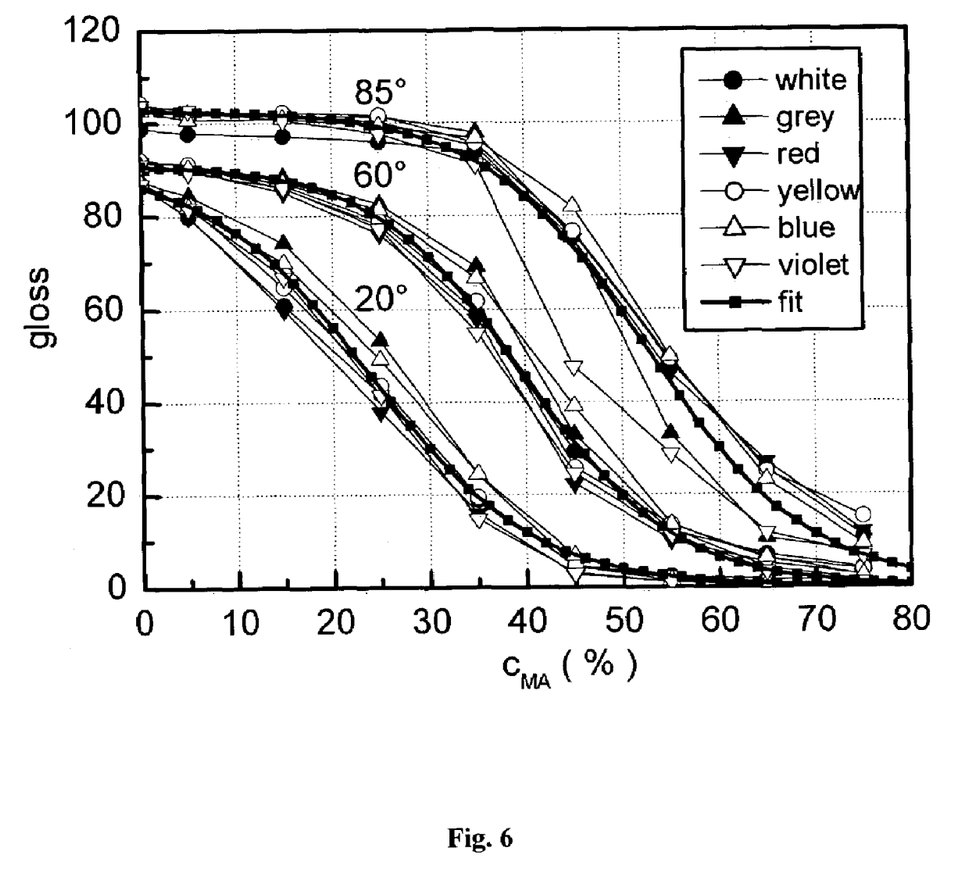
FIG. 6: Variation of surface gloss according to DIN 67530 for a typical solvent-based refinish mixing system at three different angles and for several chromatic and achromatic samples with matting agent content along with the model functions fitted to the experimental data.

FIG. 6 displays such universal functions derived for a selection of colourants of a solvent-based Refinish mixing system for all three angles of incidence (20°, 60°, 85°) recommended in DIN 67530. A commercial gloss-meter has been used for carrying out the measurements. Perhaps the most striking result of the plot is the almost universal functional behaviour of the gloss vs. matting agent content for the 20° and 60° angles. At the 85° angle a slightly wider spread of the curves is obvious. Fitting the gloss=$f\{C_{MA}\}$ to a model function this data set would certainly lead to the least accurate function of the three. When comparing the variance of the curves the 20° and 60° angle results seem to be fairly competitive in deriving the matting agent content. The maximum error $\Delta C_{MA,max}$ of the 20° gloss=$f(C_{MA})$-function is approximately 4.3%, and for the remaining two angles $\Delta C_{MA,max}$ is about 3.1% for the 60° angle and 10.6% for the 85° angle. However, in view of the variability of the matting agent content in real colour shades predominantly covering the concentration range 25–65% and the highest sensitivity of the gloss=$f(C_{MA})$ curves, the 60° function is superior to the 20° function in accuracy. Below $\Delta C_{MA,max}$=30%, the 20° function exhibits a higher sensitivity than the 60° function. To achieve the most accurate results in the whole concentration range, a combination of both universal functions of the 20° and 60° angles is recommended in this specific example.

For interpolation purposes, the experimentally determined calibration data have been described by an appropriate model function representing the data to a sufficient degree of accuracy. From the sets of gloss functions, the maximum variance on the abscissa can be estimated for any given gloss value. The maximum error $\Delta C_{MA,max}$ to be expected amounts to 7% for the 20° angle, 6% for the 60° angle, and 10% for the 85° angle. In view of the fact that most of the formulas fall into the range of $25 \leq C_{MA} \leq 65\%$, the gloss angle of 60° seems to be the best measuring geometry, since the range of highest dynamic falls within the same concentration interval.

Figure 7:
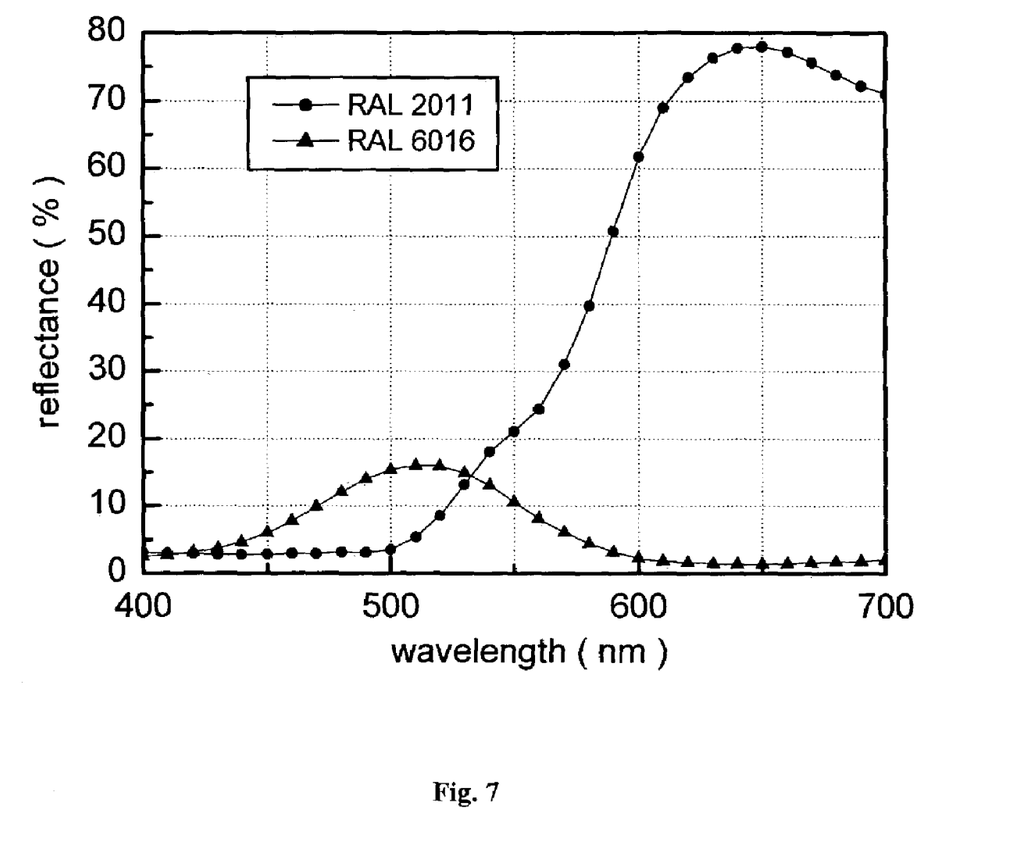
FIG. 7: Experimental reflectance functions of two semi-glossy RAL colours 2011 and 6016 within the visible spectral range.

Examples of the efficiency of the developed methodology have been worked out selecting two semi-glossy colour shades from the RAL-system (RAL 2011, RAL 6016), representing a well-accepted and established collection of colour standards in industrial applications. The experimentally determined reflectance functions of the two selected standards within the visible spectral range are depicted in FIG. 7. The commercial measurement instrument used for the colour development was equipped with a 45°/0° measurement geometry. The gloss values have been measured at the three recommended angles of 20°, 60°, and 85° using the same commercial gloss-meter (see Table II) that had been used to determine the calibration function. Both standards have been subsequently processed through the standard procedure of colour development using a set of optical material parameters derived from a set of glossy calibration panels. After identifying the appropriate pigmentation of the optimised recipe is sprayed out, remeasured and corrected in a second step using an efficient recipe correction algorithm.

The first example shows the match prediction and correction results of the semi-glossy orange RAL 2011 standard taken from the RAL 840-HR register. The formulation used to match the standard comprises the matting agent and four colourants: a red and a yellow colourant for adjusting the colour, and a black and white desaturant to adjust the lightness.

The formulation selected to match the semi-glossy green RAL 6016 standard, also taken from the RAL 840-HR register, is more complex. Besides the matting agent six colourants have to be used to achieve an acceptable spectral match: two green and two yellow pigments for adjusting the colour, and black and white desaturants to adjust the lightness.

The test results, which have been collected in Tables I and II, can be summarised as follows: (i) colour differences of the onload positions vary between 0.7 to 1.3 $\Delta E$ units, (ii) first correction steps lead to a significant improvement of colour position, (iii) the level of surface gloss could be adjusted quite precisely using the outlined calibration function, and (iv) the convergence properties are comparable to those generally observed for glossy solid colours thereby indicating that in case of matted solid colours no additional tinting steps (on the average) are needed in the colour development process.

TABLE I

Colour development information for two test examples (RAL 2011 and RAL 6016). The onload formula represents the first match. The last column specifies the first corrected formula.

| Standard | Ingredients | Onload Formula | 1. Correction |
|---|---|---|---|
| RAL 2011 | Red | 7.99 | 9.38 |
| | Yellow | 37.79 | 42.21 |
| | White | 10.26 | 10.49 |
| | Black | 0.84 | 0.94 |
| | MA | 43.11 | 36.99 |
| RAL 6016 | White | 10.51 | 10.89 |
| | Green1 | 48.34 | 48.21 |
| | Green2 | 3.31 | 0.00 |
| | Black | 2.08 | 2.40 |
| | Yellow1 | 6.66 | 6.91 |
| | Yellow2 | 2.91 | 2.71 |
| | MA | 26.19 | 28.88 |

TABLE II

Experimental results (colour and gloss information) of two test colour shades taken from the RAL system that have been worked out in a solvent-based Refinish paint line for passenger cars.

| | | L* ΔL* | a* Δa* | b* Δb* | C* ΔC* | $h_{ab}$ ΔH* | ΔE* | Gloss (20°) | Gloss (60°) | Gloss (85°) |
|---|---|---|---|---|---|---|---|---|---|---|
| RAL 2011 | STD | 59.8 | 43.5 | 69.3 | 81.8 | 57.9 | | 6.3 | 39.0 | 77.9 |
| | 1R | 0.55 | −0.40 | −0.05 | −0.25 | 0.31 | 0.68 | 2.9 | 23.0 | 68.7 |
| | 1CR | −0.06 | 0.32 | 0.15 | 0.35 | 0.32 | 0.36 | 6.4 | 38.7 | 82.5 |
| RAL 6016 | STD | 35.3 | −41.0 | 8.7 | 41.9 | 168.0 | | 34.1 | 77.0 | 92.3 |
| | 1R | −0.26 | −1.03 | 0.74 | 1.17 | −0.50 | 1.30 | 45.8 | 81.0 | 95.2 |
| | 1CR | −0.30 | 0.30 | −0.21 | −0.34 | 0.15 | 0.48 | 29.2 | 72.1 | 91.3 |

What we claim is:

1. A colour recipe calculation method for matt solid colour standards, comprising the following steps:

A) acquiring the reflection spectrum of a matt, solid colour standard using one of the following measurement geometries:

Aa) 45°/ε°—geometry with $\epsilon \geq 45°$,

Ab) d/8°—geometry with the specular component included and calculated correction of the specular component and optionally determining the colourimetric positions (L*, a*, b*) derived from the reflection spectrum, B1) matching the experimentally determined reflection spectrum, which has optionally been corrected for the specular component, using optical material parameters, stored in a pigment database, of the pigments of the available colourant system for the preparation of glossy colour shades, so obtaining a colour recipe specifying the nature of the colour-imparting pigments and the concentration thereof, or B2) comparing the experimentally determined reflection spectrum or the colourimetric positions derived therefrom with the colour recipes stored in a colour recipe database for glossy colour shades with their associated reflection spectra or colourimetric positions derived therefrom and identifying from the colour recipe database a colour recipe specifying the nature of the colour-imparting pigments and the concentration thereof which comes closest to the colour standard, C) optionally correcting the colour recipe obtained in B1) or B2) and adjusting the actual colour shade produced with the colour recipe obtained to the desired shade of the colour standard, D) measuring the degree of gloss of the matt, solid colour standard with a reflectometer conventional for gloss measurement at one or more gloss angles, E) determining the quantity of matting agent corresponding to the measured degree of gloss in the matt colour standard with the assistance of previously prepared calibration curves stored in a database for the available colourant system, which curves represent the degree of gloss measured at one or more gloss angles as a function of the quantity of matting agent in a colour recipe and F) obtaining a colour recipe to match the matt colour standard, which recipe contains the quantity of matting agent in addition to the colour recipe obtained in B1) or B2).

2. A method according to claim 1, wherein the matt, solid colour standard and the available colourant system are based on organic and/or inorganic absorption pigments.

3. A method according to claim 1, wherein the reflection spectrum of the matt, solid colour standard is acquired over a wavelength range of 400–700 nm.

4. The method according to claim 1 wherein colour shades of a vehicle coating are colour matched.

5. The method according to claim 1 wherein the colour of production coatings are colour matched.

6. A colour recipe calculation method for matt solid colour standards, comprising the following steps:

A) acquiring the reflection spectrum of a matt, solid colour standard using the following measurement geometry:

Ac) d/8°—geometry with the specular component included and with the specular component excluded and optionally determining the colourimetric positions ($L^*$, $a^*$, $b^*$) derived from the reflection spectrum, B1) matching the experimentally determined reflection spectrum with the specular component included, which has been corrected for the specular component, using optical material parameters, stored in a pigment database, of the pigments of the available colourant system for the preparation of glossy colour shades, so obtaining a colour recipe specifying the nature of the colour-imparting pigments and the concentration thereof, or B2) comparing the experimentally determined reflection spectrum with the specular component included, which has been corrected for the specular component or the colourimetric positions derived therefrom with the colour recipes stored in a colour recipe database for glossy colour shades with their associated reflection spectra or colourimetric positions derived therefrom and identifying from the colour recipe database a colour recipe specifying the nature of the colour-imparting pigments and the concentration thereof which comes closest to the colour standard, C) optionally correcting the colour recipe obtained in B1) or B2) and adjusting the actual colour shade produced with the colour recipe obtained to the desired shade of the colour standard, D1) acquiring the difference reflection spectrum of the reflection spectrum with the specular component included and the reflection spectrum with the specular component excluded, E1) determining the quantity of matting agent corresponding to the difference reflection spectrum with the assistance of previously prepared calibration curves stored in a database for the available colourant system, which curves represent the functional relationship between difference reflection spectrum and the quantity of matting agent in a colour recipe and F) obtaining a colour recipe to match the matt colour standard, which recipe contains the quantity of matting agent in addition to the colour recipe obtained in B1) or B2).

7. A method according to claim 6, wherein the matt, solid colour standard and the available colourant system are based on organic and/or inorganic absorption pigments.

8. A method according to claim 6, wherein the reflection spectrum of the matt, solid colour standard is acquired over a wavelength range of 400–700 nm.

9. The method according to claim 6 wherein colour shades of a vehicle coating are colour matched.

10. The method according to claim 6 wherein the colour of production coatings are colour matched.

* * * * *